United States Patent [19]

Beentjes

[11] 4,438,653

[45] Mar. 27, 1984

[54] SUBLANCE FOR MEASURING AND/OR SAMPLING IN A METALLURGICAL FURNACE

[75] Inventor: Nicolaas H. Beentjes, Uitgeest, Netherlands

[73] Assignee: Estel Hoogovens B.V., Netherlands

[21] Appl. No.: 395,710

[22] Filed: Jul. 6, 1982

[30] Foreign Application Priority Data

Jul. 10, 1981 [NL] Netherlands .................... 8103306

[51] Int. Cl.³ .............................................. G01N 1/10
[52] U.S. Cl. ................ 73/863.11; 73/DIG. 9; 73/864.59; 374/140
[58] Field of Search ......... 73/DIG. 9, 863.11, 864.59; 374/140; 136/234

[56] References Cited

U.S. PATENT DOCUMENTS

| 3,643,508 | 2/1972 | Schneider | 73/863.11 X |
| 3,717,034 | 2/1973 | Dukelow | 374/140 |
| 3,813,943 | 6/1974 | Fradeneck | 374/140 |
| 3,889,538 | 6/1975 | Fingerle | 73/863.11 |
| 3,967,505 | 7/1976 | Feichtinger | 73/DIG. 9 X |
| 4,015,475 | 4/1977 | Pluschkell et al. | 73/864.59 X |
| 4,141,249 | 2/1979 | Ishikawa et al. | 73/DIG. 9 X |
| 4,272,989 | 6/1981 | Rymarchyk et al. | 374/140 X |

FOREIGN PATENT DOCUMENTS

| 2460122 | 6/1976 | Fed. Rep. of Germany | 73/863.11 |
| 147966 | 4/1981 | German Democratic Rep. | 73/863.11 |
| 2045928 | 11/1980 | United Kingdom | 73/DIG. 9 |
| 298655 | 4/1971 | U.S.S.R. | 73/DIG. 9 |

OTHER PUBLICATIONS

Patents Abstracts of Japan, vol. 2, No. 31, Feb. 27, 1978, p. 4318 C 77, "Sampling and Temperature Measuring With Sublance".

Primary Examiner—Gerald Goldberg
Assistant Examiner—Tom Noland
Attorney, Agent, or Firm—Stevens, Davis, Miller & Mosher

[57] ABSTRACT

A sublance for use in performing measurements and/or taking samples in a metallurgical furnace, which has an elongate outer body (3), (11) having at its upper end a suspension structure (4), and at its lower end (12) a probe (10). Near the upper end, the body is divided by a rotational coupling (8), (9) into two parts, the lower part 11 being relatively rotatable about the longitudinal axis, so that bending distortion of the lance in use can be reversed by turning the lance through 180°. To achieve a simple construction, the inner and intermediate tubes (15), (14) within the lance are not rotationally divided but extend within the rotatable outer part (11) to the lower end (12) where the inner tube (15) is rotationally coupled to the probe.

4 Claims, 4 Drawing Figures

SUBLANCE FOR MEASURING AND/OR SAMPLING IN A METALLURGICAL FURNACE

BACKGROUND OF THE INVENTION

1. Field of the Invention

The invention relates to a sublance for use in performing measurements and/or taking samples in a metallurgical furnace. The principal use of such a lance is in a metallurgical furnace in which there is a main lance for supplying oxygen, where the sublance which has a probe at its lower end is dipped into a hot metal bath and withdrawn again.

Particularly, the invention will be described here to its application to a steel converter of the type in which liquid pig iron is converted to steel by means of top-blown oxygen from a main lance. However analogous applications of the invention are possible in metallurgical processes in other types of metallurgical furnaces.

2. Description of the Prior Art

In order that it is possible to monitor the progress of the refining process in the steel furnace and control it when necessary during the oxygen blowing, a sublance as described above is often used. During oxygen blowing, or during a pause in the oxygen blowing, the sublance is moved down towards the metal bath parallel to the main lance so that the probe can reach into the bath. The probe may be equipped with means for measuring the bath temperature and/or analyzing the concentration of certain elements such as carbon and oxygen in the bath. These measured values can then be transmitted from the probe to the exterior of the furnace via a cable extending through the sublance. It is also possible to use a probe in the form of a sample vessel, so that the sublance can take a sample from the pool, for analysis outside the furnace. The technique for the use of sublances to carry out such measurements and/or take samples is described in the literature.

A difficulty encountered in the use of such a sublance is that, if the sublance is lowered during oxygen blowing it is heated asymetrically by the furnace. This causes the sublance to bend, so that it may be useful for only a few measurements, or even only one measurement. A conventional method of overcoming this difficulty is to remove the lance from its suspension after use and to bend it straight elsewhere. It can then be remounted and used again.

The availability of the lance is thus limited, and operating and maintaining it require considerable labour. In particular, if the lance is of the liquid-cooled type, the connections for the liquid cooling need to be removed and replaced each time it is bent straight.

Another difficulty in the conventional use of the sublance is that, as a result of its bending, the data obtained with it have limited reproducibility.

U.S. Pat. No. 4,141,249 describes a construction in which the sublance is mounted so as to be rotatable about its axis so that, after the sublance has been used once, resulting in its being bent, it can be rotated through 180° so that the bend is reversed. During subsequent use of the lance, it will be bent back again by the heating more or less to the original straight condition.

Typically the sublance has, within its outer body, several concentric passages, e.g. for downward and return flows of cooling fluid and for a cable connected to the probe. In the lance of U.S. Pat. No. 4,141,249, this leads to a rather complex and difficult arrangement at the connections to the rotatable lance. Because of the operational environment of the lance, these connections must not be delicate or liable to failure.

SUMMARY OF THE INVENTION

The object of the present invention is to provide a sublance with which the technique of rotation through 180° to reverse its bending can be used but which nevertheless can be of simple and robust construction.

According to the invention, the outer tubular member of the sublance is divided by a rotational coupling so that its lower part is rotatable, but inner and intermediate tubular members are not rotationally subdivided but extend non-rotatably to the lower end of the lance. Thus only a simple rotational coupling in the outer tube is required, and the longitudinal passages within the lance are not affected.

At the lower end of the lance, the inner tube is preferably connected to the probe by a rotational connection, while the lower end of the intermediate tube may be free. The intermediate tube may therefore lose concentricity with the outer tube, but this need not for example unduly affect the flow of coolant.

In a sublance of the liquid-cooled type the rotatable coupling between the parts of the outer tube must naturally be provided with a seal to prevent leakage of the coolant.

In the invention, the method of using the sublance is of interest, particularly its use in a metallurgical furnace of the type with a main lance to introduce oxygen, where periodically the sublance with its probe is dipped into the hot metal bath and withdrawn again. Suppose that after each measurement with the probe, the lower part of the outer tube of the sub-lance is turned, so that a situation is reached in which at each measurement the lance bends in a similar way. It can be the case that the lance is turned during the course of a measurement, so that the bending can be compensated directly. The preferred method of operation is one which requires as little manipulation of the auxiliary lance as possible, although good results are still obtained. This may be achieved if after every two descents of the sublance to the hot metal bath, the outer tube of the sub-lance is turned through about 180°, the first such rotation taking place after the first use of the sublance. If the lance is bent after the first use, then after this rotation it will return to the correct condition after the first subsequent use, and the second subsequent use will bring it to a reversed direction. The outer tube is then turned again, after which the sequence repeats itself. It will be seen that in this way all demounting and remounting operations of the lance may become superfluous.

BRIEF DESCRIPTION OF THE DRAWINGS

The preferred embodiment of the invention will now be described by way of non-limitative example with reference to the accompanying drawings, in which.

DESCRIPTION OF THE PREFERRED EMBODIMENTS

Figure 1A:
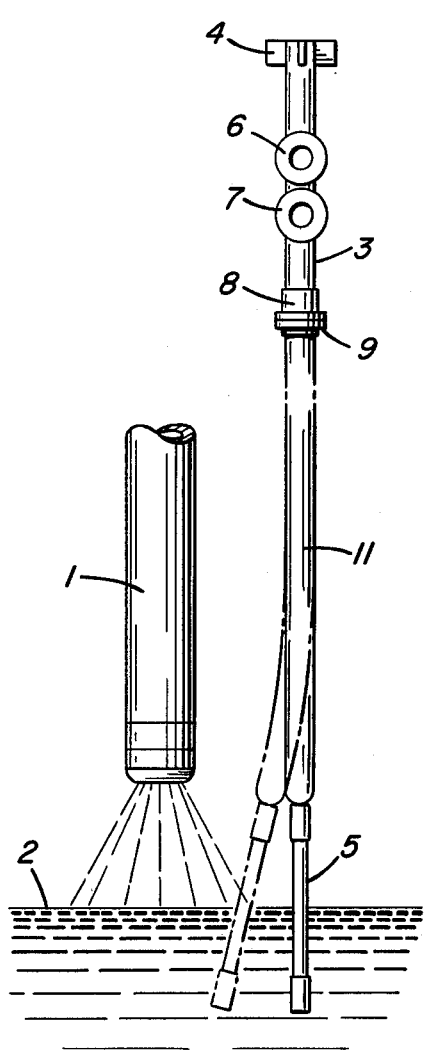
FIGS. 1A and 1B are diagrammatic views of the sublance embodying the invention in different phases of its process.
Figure 1B:
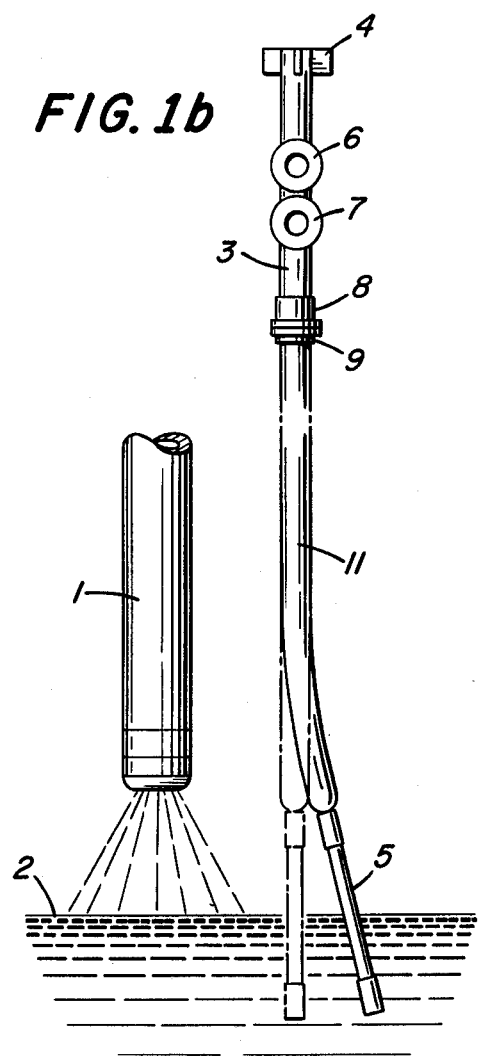

FIGS. 1A and 1B show a main lance 1 which is blowing oxygen onto a hot metal bath 2. The sublance 3 embodying the invention is shown in its lowest position extending generally parallel to the main lance 1, with a probe 5 carried at its lower end dipping into the bath.

At the top end of the sublance 3 there are flanges 4 which serve for suspension of the lance 3 in the drive system used to move it vertically. This drive system is not shown since it is of a conventional type used to lower and raise sublances. An inlet 6 and outlet 7 for cooling liquid are connected near the upper end of the lance 3, so that the lance is cooled, as far down as the mounting means for the probe 5, by a flow of coolant within the lance.

Near the upper end of the sublance 3 its outer tubular member or body is divided and the two parts thereof are joined by a coupling formed by coupling parts 8,9. As shown in more detail below, the coupling parts 8,9 can be rotated with respect to each other about the vertical axis and they are provided with a gasket to prevent leakage of the coolant. The outer tube of the sublance 3 thus has a lower part 11 which is rotatable about the longitudinal axis of the lance with respect to the suspension flanges 4.

The operation of this sub-lance will be described next. FIG. 1A indicates, by full lines, the position of the lance before oxygen is blown on to the bath. The sublance is straight and upright at that time. During blowing, the sublance is heated at one side more than the other in such a way that it bends towards the blowing location, and reaches the position indicated by the broken lines.

The sublance is now moved upwards, and in the raised position the coupling part 9 is rotated by 180° with respect to the coupling part 8, so that the sublance is brought back to the lowered position again, it has the position indicated by the full lines in FIG. 1B. As the bath is blown again, the lance bends back until it is straight again, as indicated by the broken lines in FIG.1B.

It will be clear that, after the termination of the second blowing phase and at the subsequent raising and lowering of the sublance, there is no requirement for a mutual rotation of the coupling parts 8 and 9, since the lance is now in the position and shape which it had in the initial position of FIG. 1A. Only after a further subsequent use of the lance will it be bent again and the two parts of the outer tube of the lance must be mutually rotated. If this scheme is followed, it is thus sufficient if the lower part of the outer tube of the sublance is turned through 180° after every two uses.

Figure 2:
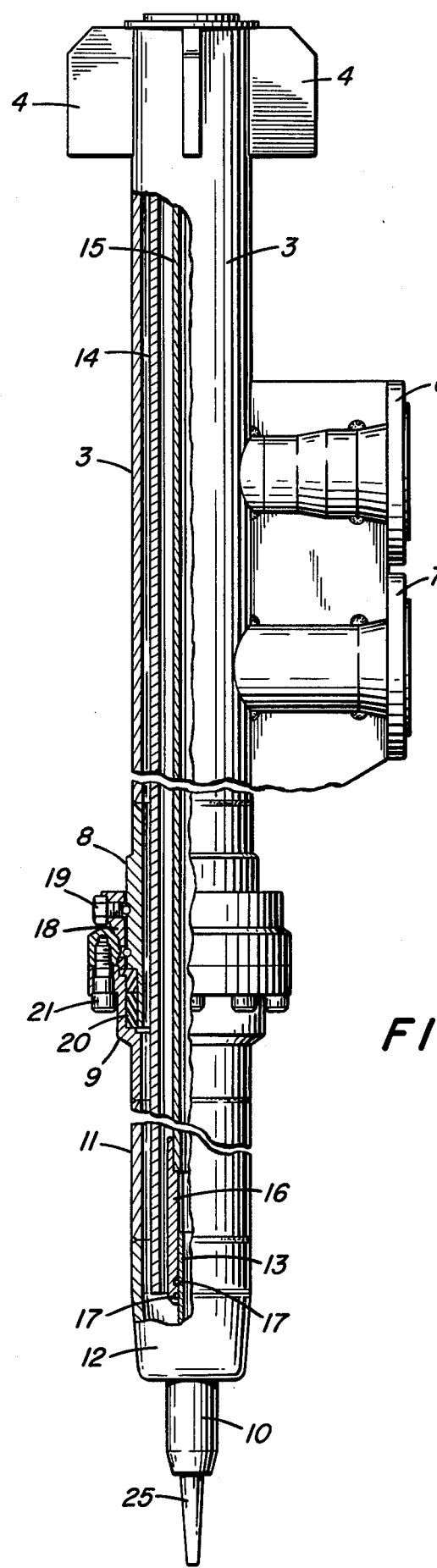
FIG. 2 shows the sublance embodying the invention partly in elevation and partly in longitudinal section.

In FIG. 2 the reference numbers of FIGS. 1A and 1B are used to indicate corresponding elements.

FIG. 2 shows that, within the outer sleeve 3 tube with the rotatable lower part 11, an intermediate tube 14 and an inner tube 15 are located, these tubes 14,15 being secured at the upper end of the sublance 3. The tubes 14,15 thus form, with the outer tube, two concentric annular spaces downward and return flow of cooling fluid, which spaces are appropriately connected to the inlet and outlet connections 6,7 (which are on the non-rotatable upper part of the outer tube). The lower end of the intermediate tube 14 is free, allowing free communication of the annular spaces at that end of the lance. The space within the inner tube 15 may be used for a cable extending to the probe 5 mounted on the lower end of the lance.

The probe 5 is omitted from FIG. 2. At the lower end of the sublance 3 is an end-cap 12 secured to the rotatable part 11 of the outer tube. This end-cap carries an upwardly extending tube 13 which is received by a tubular bottom extension 16 of the inner tube 15, the tube 13 being rotatable within the extension 16 and sealed thereto by two liquid-tight sealing rings 17. FIG. 2 shows a mounting member 10 for the probe 5 and a contact block 25 extending from it. The member 10 is fixed to the end-cap 12.

The end-cap 12 thus non-rotatably mounts the probe 5 on the rotatable part 11 and makes a rotatable coupling of the probe to the inner tube 15 at the lower end of the lance 3.

The coupling parts 8 and 9 are sealed liquid-tightly against one another by means of the gasket 20. A ring 18 is rotatable around part 8, being carried by ball bearings sealed by the screws 19 and running in a groove in the part 8. The coupling part 9 is secured against the ring 18 by screws 21.

Figure 3:
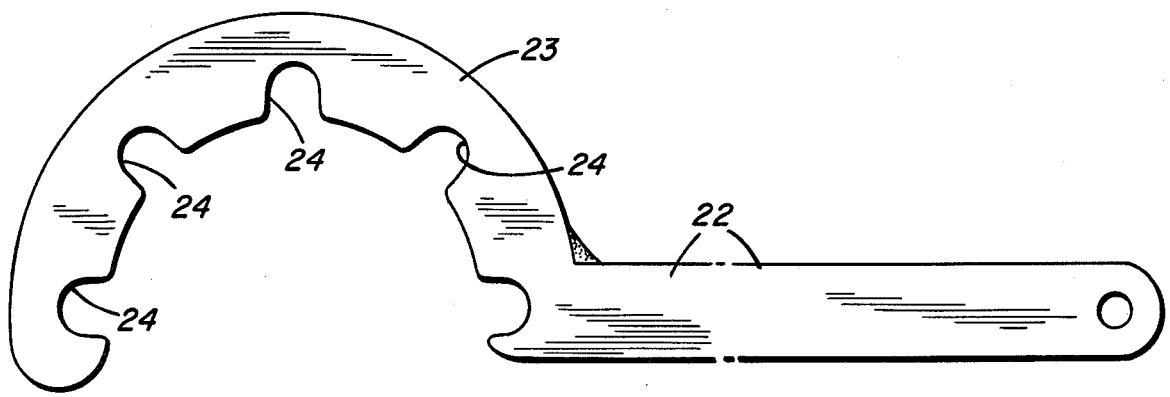
FIG. 3 shows an accessory used for turning outer tube of the sublance.

The circle of screw heads 21 also serves as a grip for use in turning the tube part 11 relative to the coupling part 8. FIG. 3 shows a key designed for this purpose, consisting of a handle 22 and a semi-circular part 23 with recesses 24. The recesses 24 correspond to the screw heads 21.

Rotation of the outer tube part 11 does not therefore cause rotation of the intermediate and inner tubes 14,15, which are not rotationally divided. When the outer tube 11 is distorted as shown in FIGS. 1A and 1B and when it is rotated through 180°, the inner tube 15 is constrained to retain its concentricity in the outer tube by the connection 13,16. The intermediate tube 14 is not so constrained and may therefore lose its concentricity, but this does not adversely affect the flow of coolant.

What is claimed is

1. In a sublance for use in monitoring the operation of a metallurgical furnace, comprising an elongate outer tubular member an elongate intermediate tubular member located within said outer member and an elongate inner member located within said intermediate member, each said member extending from an upper end of the sublance, at which there are suspension means for suspending the sublance in use and connections for communication with the interior spaces of the sublance, to a lower end of the sublance at which a probe is mounted on the sublance, the sublance further including a rotational coupling so that the probe is rotatable about a longitudinal axis of the sublance relative to the suspension means the improvement that:

said rotational coupling is located so as to divide only said outer tubular member close to said upper end, so that an upper part of said outer member to which part said connections are attached, is fixed relative to the suspension means and a lower part of said outer member on which part said probe is mounted, is rotatable about the longitudinal axis relative to the suspension means and also relative to said inner and intermediate tubular members which are not rotationally divided.

2. A sublance according to claim 1 wherein the probe is connected to said inner tubular member at the lower end of the sublance by a connection permitting rotation of the probe relative to the inner member so that the inner tubular member is maintained in a concentric position relative to the outer member.

3. A sublance according to one of claims 1 or 2 wherein the lower end of said intermediate tubular member is free and is constrained to remain concentric relative to the outer member.

4. A sublance for monitoring the operation of a metallurgical furnace, comprising
   (a) an elongate outer tubular member having an upper end and a lower end and divided close to said upper end into an upper part and a lower part, the sublance having a longitudinal axis extending from said upper end to said lower end,
   (b) suspension means for mounting the sublance in use, connected to said upper part of said outer member at said upper end,
   (c) a rotational coupling connecting said upper part of the outer member to said lower part thereof so as to permit rotation of said lower part relative to said upper part about said longitudinal axis,
   (d) a probe mounted on said outer member at the lower end thereof,
   (e) an intermediate elongate tubular member located within said outer member and extending, without a rotational coupling, from said upper end to said lower end thereof,
   (f) an inner tubular member located within said intermediate member and also extending, without a rotational coupling from said upper end to said lower end, the three tubular members thus defining concentric spaces within the sublance,
   (g) connection means at said upper part of the outer member for communication with spaces within the sublance,
   (h) a coupling connecting said inner member to said probe and permitting relative rotation of the probe relative to the inner member about said axis.

* * * * *